United States Patent [19]

Giles

[11] Patent Number: 4,971,911

[45] Date of Patent: Nov. 20, 1990

[54] PROCESS AND APPARATUS FOR MEASURING THE ALCOHOL CONTENT OF DAMPING FLUID AND ALCOHOL DAMPING SYSTEMS IN OFFSET PRINTING PRESSES

[75] Inventor: Jorge M. R. Giles, Wiesbaden, Fed. Rep. of Germany

[73] Assignee: Miller-Johannisberg Druckmaschinen GmbH, Wiesbaden-Briebrich, Fed. Rep. of Germany

[21] Appl. No.: 395,251

[22] Filed: Aug. 17, 1989

[30] Foreign Application Priority Data

Aug. 20, 1988 [DE] Fed. Rep. of Germany ....... 3828325

[51] Int. Cl.$^5$ ................................................ G01N 1/22
[52] U.S. Cl. ...................................... 436/55; 436/131; 436/177; 436/181; 137/3; 137/93
[58] Field of Search ............... 422/68, 69, 80; 436/55, 436/131, 132, 177, 181; 55/53; 137/3, 93

[56] References Cited

U.S. PATENT DOCUMENTS

| | | | |
|---|---|---|---|
| 3,198,000 | 8/1935 | Schlageter | 436/181 X |
| 3,582,274 | 6/1971 | Keyes | 436/132 |
| 4,683,211 | 7/1987 | Onizuka | 436/181 |
| 4,849,178 | 7/1989 | Azuma | 436/164 X |

Primary Examiner—Alan Cohan
Attorney, Agent, or Firm—Carothers & Carothers

[57] ABSTRACT

A process and apparatus for measuring the alcohol content of damping fluid for alcohol damping systems such as in offset printing presses for the purpose of keeping the alcohol concentration at a constant set value by injecting alcohol into the damping fluid in addition to the constant or parameter dependent addition of alcohol.

19 Claims, 1 Drawing Sheet

U.S. Patent  Nov. 20, 1990  4,971,911
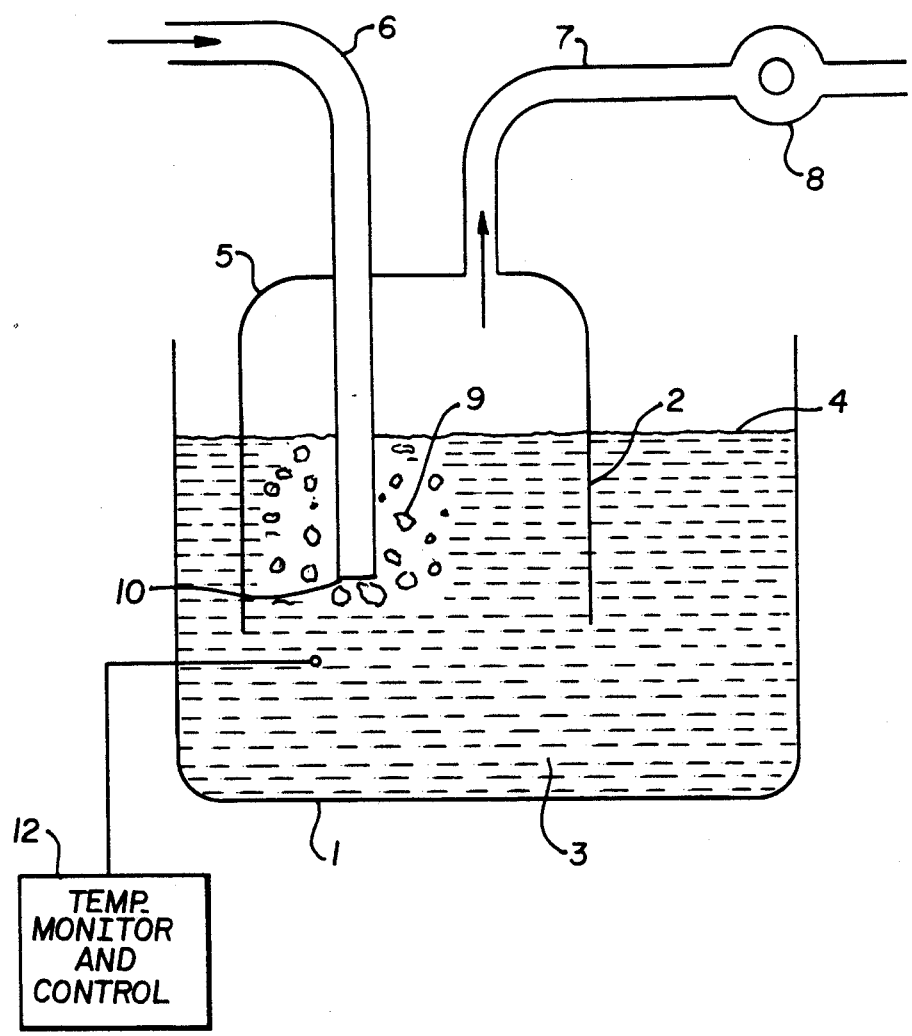

PROCESS AND APPARATUS FOR MEASURING THE ALCOHOL CONTENT OF DAMPING FLUID AND ALCOHOL DAMPING SYSTEMS IN OFFSET PRINTING PRESSES

BACKGROUND OF THE INVENTION

The invention relates to a process and apparatus for measuring the alcohol content of the damping fluid for alcohol damping systems such as those used in offset printing presses, in order to keep the alcohol content or concentration at a constant set value. This is done by injecting alcohol into the damping fluid, in addition to the conventional addition of alcohol as determined by experimental values or an addition of alcohol according to parameters set through experimental values. This additional injection of alcohol results in a sensitive adjustment of the set value, while the constant or parameter dependent addition of alcohol results in a rough adjustment.

The measurement of alcohol content in damping agents of prior art alcohol damping systems in offset printing presses has involved measuring the density of the damping agent through hydrometering or aerometering for example. This type of measurement is not very exact because it does not take into account that the specific weight or density of the damping agent does not depend only on the alcohol content (usually isopropyl alcohol, i.e.: using 2-propyls), but also to a large extent on the amount of additives utilized for the purpose of maintaining a specific pH value, typically in the range of 4 to 6.5 for example. Generally, such additives are supplied to the damping agent for the protection of the platen and surface substances including antimicrobial ingredients, complexing agents to compensate for high water hardness, anticorrosive inhibiting substances, and others.

Such additive substances influenece the specific weight of the damping medium in such a way that the alcohol content determined by hydrometer may be 50% to 100% higher than the actual alcohol content determined by chemical analysis. Excessive alcohol content is not only a waste of rather costly alcohol, it also increases immission, etching of the color and a generally less than optimal print work. Consequently it is desirable to work with the lowest possible alcohol content, preferably in the range of 6%, for example. At such low levels of alcohol content, it is absolutely necessary to stay as close as possible to the set value, since the impact of a 1% alcohol content variation is far greater at lower set values than if the set value were higher, for example 15%.

BRIEF SUMMARY OF THE INVENTION

According to the present invention, damping agent or fluid kept at constant temperature in a partially filled, enclosed top container has compressed air admitted in the area above the fluid to form a gas-water-vapor mixture above the level of damping agent, which mixture is measured with a device of known art (such as heat tone measurement, chemosorption on metal oxide semi-conductors, flame ionization detectors or by non-contact with spectroscopic or radiation absorption processes) for its content of combustible gas. Since the only combustible gas in the mixture is alcohol vapor, the measurement provides indication of the alcohol content.

The gas-water-vapor mixture is formed by injecting air into the damping medium in the container so that air bubbles rising in the damping agent have a specific water vapor and alcohol saturation pressure when they reach the upper surface level of the damping medium, and the saturation vapor pressure of alcohol at a constant temperature is directly proportional to the alcohol concentration, which is a known law of physical chemistry.

Devices for the measurement of the content of combustible gas or vapor in a gas vapor mixture are known in many different forms, and have been in oil tankers, drilling platforms, mines (for the detection of methane gas explosion danger) and in many other applications. Keeping the damping medium temperature constant does not present additional problems, since the damping medium is cooled to a specific temperature in the damping medium processor. The quality of alcohol to be added to the damping medium at a constant or parameter determined temperature for rough adjustment of alcohol content depends, as always, on the type of machine, the printing speed, the subject, the printer platen type, the printing material and the outside temperature impacting on the vaporized quantity of alcohol.

The apparatus to perform the process according to the invention is as described hereinbelow and the required measuring devices according to this invention may be any of a variety of already available and well tested apparatus.

The invention can also be realized in such a way, that even if the temperature of the fluid is not kept constant, the temperature thereof may be measured and taken into account in determining the alcohol concentration in the damping medium.

The gas-vapor mixture can be formed in a percolator chamber or washer. It is also possible to form the gas-vapor mixing by evaporation on a free fluid surface, on a fluid surface wetted with a fluid, or on some other fluid surface. Furthermore, it is also possible to form the gas-vapor mixture by evaporation through a membrane. These and other aspects of the invention will be more fully apparent upon consideration of the following detailed description, reference being made therein to the accompanying drawings in which the sole FIGURE is a schematic depiction of one type of device for execution of the process according to the present invention.

In a random container 1, such as a large container in a central damping fluid processor for a variety of printing presses, or alternatively the damping agent boxes of a damping system, there is a quantity of damping fluid 3. In container 1 a downwardly opening bell shaped container or percolating chamber 2 is inserted into the damping fluid 3 to form a space within container 2 and above the upper surface of damping fluid 3, which space is enclosed at the top by a cover portion 5 of container 2. The interior of container 2 has compressed air admitted through a line or conduit 6 which extends into the damping fluid 3, air emitted from the lower open end of line 6 forms bubbles 9 which rise within inner container 2. When bubbles reach the damping agent surface 4 level and break through, they contain a water vapor-alcohol vapor mix with an alcohol concentration that is equal to the alcohol concentration of the damping fluid 3. A part of the water vapor-alcohol vapor mixture is fed through a line or conduit 7 to a suitable measuring device 8, which measures the content of combustible gas in the mixture. Device 8 may also include apparatus for calculating alcohol content. As the only combustible gas in the mixture is alcohol vapor, the measurement of combustible gas provides indication of the alcohol concentration of the damping fluid 3.

A suitable temperature monitoring and control apparatus 12, preferably is also provided to maintain a constant temperature of the damping fluid 3 within container 1. Additionally, the lower open end of line 6 may include a diffuser 10, or similar apparatus to diffuse the emitted air flow into finely divided bubbles. These and other alternatives and modifications are contemplated, and certainly such would also occur to others versed in the art, once apprised of my invention. Accordingly, it is intended that the invention be construed broadly and limited only by the scope properly attributable to the claims appended hereto.

I claim:

1. A apparatus for measuring the alcohol content of damping fluid in an alcohol damping system of an offset printing press comprising:
    means for feeding gas to such damping fluid;
    means for mixing such gas with such damping fluid;
    collection means for collecting such gas after mixing thereof with such damping fluid; and
    measuring means for measuring the alcohol content of such collected gas.

2. The apparatus as set forth in claim 1 additionally including means for keeping such damping fluid at a constant temperature.

3. The apparatus as set forth in claim 1 wherein said measuring means includes temperature monitoring means for measuring the temperature of such damping fluid and calculating means for calculating the alcohol content of such damping fluid from the measured alcohol content of such gas and the temperature of such damping fluid.

4. The apparatus as set forth in claim 1 wherein said measuring means includes a tone measurement device to measure such alcohol content.

5. The apparatus as set forth in claim 1 wherein said measuring means includes means for measuring chemosorption on metal oxide semi-conductors to measure such alcohol content.

6. The apparatus as set forth in claim 1 wherein said measuring means includes flate ionization detector means to measure such alcohol content.

7. The apparatus as set forth in claim 1 wherein said measurement means includes spectrometer means for measuring such alcohol content.

8. The apparatus as set forth in claim 1 wherein said means for feeding gases includes means immersed within such damping fluid which divides such gas into finally divided bubbles which subsequently rise through such damping fluid.

9. The apparatus as set forth in claim 8 wherein said means for feeding gases is immersed within such damping fluid within a percolating chamber means which is effective for mixing such gas with such damping fluid.

10. The apparatus as set forth in claim 1 wherein said means for feeding gas includes a gas feeder for feeding such gas to a space above the upper surface of the damping fluid in a damping fluid chamber.

11. The apparatus as set forth in claim 1 wherein said means for feeding gas includes a gas feeder and a separate wetted surface which is adapted to be wetted with such damping fluid.

12. The apparatus as set forth in claim 1 wherein said means for feeding gas includes a gas feeder for feeding gas to a membrane that is in contact with such damping fluid.

13. An apparatus for measuring the alcohol content of damping fluid in an alcohol damping system for an effect printing press for the purpose of controlling or stabilizing the damping fluid alcohol content at a set value by injection of alcohol into the damping fluid in addition to the constant or parameter dependent alcohol addition thereto comprising:
    a container means (2) having an enclosed top (5);
    means (1) for maintaining said container (2) partially filled with damping fluid (3);
    temperature monitoring and control means (10) for keeping said damping (3) at a constant temperature;
    compressed air inlet means (6) for directing compressed into said damping fluid (3) within said container (5) for forming a gas-water vapor mixture within said container (5) above said upper surface (4) of said damping fluid (3); and
    measuring means (8) for measuring the content of combustible gas within said gas-water vapor mixture.

14. In a damping fluid handling system for handling damping fluid in an offset printing press, the method of stabilizing the alcohol content of such damping fluid at a predetermined value comprising the steps of:
    providing a volume of damping fluid;
    feeding air into contact with said damping fluid;
    maintaining sufficient contact of said air with said damping fluid to form a gas-water vapor mixture;
    extracting said gas-water vapor mixture from said damping fluid;
    measuring the alcohol content of said gas-water vapor mixture; and
    injecting alcohol into the damping fluid of said damping system in accordance with the requirements for additional alcohol injection as indicated by said measuring step.

15. The method as set forth in claim 14 including the additional step of maintaining the temperature of said damping fluid constant.

16. The method as set forth in claim 14 wherein said measuring step includes measuring the temperature of said damping fluid and utilizing said measurement of temperature of said damping fluid in conjunction with said measurement of alcohol content to determine the said requirement for injection of additional alcohol into said damping fluid.

17. The method as set forth in claim 14 wherein the contact between the air and the damping fluid is contact on a free fluid surface with formation of said mixture resulting through evaporation from said free fluid surface.

18. The method as set forth in claim 14 wherein the contact of air with the damping fluid occurs on a surface wetted with damping fluid and the formation of the gas-water vapor mixture includes evaporation from the wetted surface.

19. The method as set forth in claim 14 wherein the contact of air with the damping fluid occurs in a membrane which is in contact with the damping fluid and the formation of the gas-water vapor mixture includes evaporation through the membrane.

* * * * *